United States Patent
Beier et al.

(10) Patent No.: US 6,673,544 B1
(45) Date of Patent: Jan. 6, 2004

(54) METHOD FOR THE LIGHT-CONTROLLED SYNTHESIS OF BIOCHIPS

(75) Inventors: Markus Beier, Heidelberg (DE); Stefan Matysiak, Heidelberg (DE); Jorg Hoheisel, Wiesloch (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 0 days.

(21) Appl. No.: 09/868,540

(22) PCT Filed: Dec. 17, 1999

(86) PCT No.: PCT/DE99/04051

§ 371 (c)(1),
(2), (4) Date: Nov. 28, 2001

(87) PCT Pub. No.: WO00/35931

PCT Pub. Date: Jun. 22, 2000

(30) Foreign Application Priority Data

Dec. 17, 1998 (DE) ................................ 198 58 440

(51) Int. Cl.[7] .......................... C12Q 1/68; C07H 21/02; A01N 25/00
(52) U.S. Cl. .............................. 435/6; 435/94; 536/25.3; 536/26.1; 536/27; 536/28.5; 536/55.3; 514/789
(58) Field of Search ................ 536/55.3, 25.3, 536/28.5, 26.1, 27; 435/6, 94; 514/789

(56) References Cited

U.S. PATENT DOCUMENTS

| | | | | |
|---|---|---|---|---|
| 5,539,082 A | * | 7/1996 | Nielsen et al. | 530/300 |
| 5,744,305 A | * | 4/1998 | Fodor et al. | 536/25.3 |
| 5,763,599 A | * | 6/1998 | Pfleiderer et al. | 536/55.3 |
| 5,981,734 A | * | 11/1999 | Mirzabekov et al. | 536/25.3 |
| 6,153,744 A | * | 11/2000 | Pfleiderer et al. | 536/25.3 |

FOREIGN PATENT DOCUMENTS

| | | |
|---|---|---|
| DE | 36 06395 A1 | 3/1987 |
| WO | WO 96/18634 | 6/1996 |
| WO | WO 97/44345 | 11/1997 |

OTHER PUBLICATIONS

Chemical Abstracts 129, p. (1998).
Fodor, et al., "Light–Directed, Spatially Addressable Parallel Chemical Synthesis," *Research Article* pp. 767–773 (1991).
Falbe and Regitz, Römpp Chemie Lexikon pp. 419, 3060.
Giegrich, et al. "New Photolabile Protecting Groups in Nucleoside and Nucleotide Chemistry—Synthesis, Cleavage Mechanisms and Applications," *Nucleosides and Nucleotides*, 17(9): 1987–1996 (1998).
Pfister, et al. "The 2–(4–Nitrophenyl)ethylsolfonyl (Npes) Group: A New type of Protection in Nucleoside Chemistry," *Helvetica Chimica Acta* 78:1705–1737 (1995).
Pease, et al., "Light–generated oligonucleotide arrays for rapid DNA sequence analysis," *Proc. Natl. Acad. Sci. uSA* 915022–5026 (1994).
Weiler and Hoheisel, "Combining the Preparation of Oligonucleotide Arrarys and Synthesis of High–Quality Primers," *Analytical Biochemistry* 243:218–227 (1996).

* cited by examiner

Primary Examiner—Jezia Riley
(74) Attorney, Agent, or Firm—Albert P. Halluin; Viola T. Kung; Howrey, Simon, Arnold & White, LLP

(57) ABSTRACT

The present invention relates to a method for the photolithographic synthesis of biochips in which photolabile protective groups of the 2-(2-nitrophenyl)ethyl type are used, whereby the irradiation step that is common in the photolithographic chip synthesis is carried out in the presence of a base, preferably a secondary or uerriary base.

10 Claims, 3 Drawing Sheets

(2 of 3 Drawing Sheet(s) Filed in Color)

Photolithographic DNA-Chip Synthesis

NPPOC irradiation : 5 min, 365 nm, 100 W Hg-lamp
ScanArray 3000, LP 100 %, PMT 75%

0.005 M DBU acetonitrile

10 % H$_2$O / MeOH dry

Photolithographic DNA-Chip Synthesis irradiation : 5 min, 365 nm, 100 W Hg-lamp
ScanArray 3000, LP 100 %, PMT 75%

0.05 M DBU 0.5 M DBU 0.05 M diisopropyl-
ethylamine 0.05 M piperidine

METHOD FOR THE LIGHT-CONTROLLED SYNTHESIS OF BIOCHIPS

This application is a National Stage of International Application PCT/DE99/04051, filed Dec. 17, 1999; which claims the priority of DE 198 58 440.7, filed Dec. 17, 1998.

FIELD OF THE INVENTION

The present invention relates to a method for the light-controlled (photolithgaphic) synthesis of biochips.

BACKGROUND OF THE INVENTION

The field concerning the synthesis of oligonucleotides and DNA or RNA chips has been booming for several years, and efficient methods are required in this connection.

Synthetic DNA fragments (oligonucleotides) are nowadays prepared almost exclusively in accordance with to the phosphite amide method. This preparation is made with the aid of what is called DNA synthesizers. After inputting the target sequence, these machines automatically synthesize the desired DNA oligomer. For this purpose, the DNA synthesizer has a computer-controlled programming determining in which order certain reagents are pumped onto the synthesis column where the actual synthesis of the DNA oligomer takes place in the solid phase on glass beads of e.g. controlled pore glass (CPG). The reagents include inter alia the 4 (protected) phosphite amides for the 4 bases (adenine, cytidine, guanosine, thymine), the catalyst (usually tetrazole), an oxidizing agent (usually iodine), capping reagent A & B (usually acetic anhydride, N-methylimidazole), and detritylation reagent (usually trichloroacetic acid). A reaction cycle consists of the following sequence:

| | |
|---|---|
| (1) detritylation | cleavage of the temporary 5'-O-dimethoxytrityl protecting groups by trichloroacetic acid; |
| (2) condensation | the phosphite amide corresponding to the target sequence is condensed onto the released 5'-hydroxyl function; this is done with the aid of the acidic catalyst (tetrazole); |
| (3) oxidation | the unstable phosphite triester linkage (P-III) is converted by oxidation with iodine into a stable phosphorus triester (P-V); |
| (4) capping | the 5'-hydroxyl functions which did not react in the preceding step shall be trapped by an acetylation step (acetic anhydride + N-methylimidazole); this shall prevent uncontrolled growth of the DNA strand. |

Steps (1) to (4) are then repeated until the target sequence has been obtained.

The initiator nucleoside, which carries preferably a 5'-O-dimethoxytrityl protecting group, is usually found on the support already, so that the detritylation step is started. As soon as the target sequence has been obtained, the phosphate protecting groups and the protecting groups of the exocyclic amino functions of the heterobases have to be cleaved. This is usually done by means of ammonia. The cleavage of the oligomer from the support also takes place simultaneously with ammonia, so that the fully synthesized oligomer is then in the ammonia cleavage solution. Having evaporated the ammonia solution, the target oligomer is obtained.

The step decisive for the quality of the synthesis is the condensation, since all of the other steps (detritylation, oxidation, capping) proceed quantitatively. The condensation is carried out in the absolute absence of humidity. Condensation yields of up to 99% can be achieved.

The synthesis of nucleic acid chips on support surfaces is carried out according to an analogous method, so that, in principle, the below described chip synthesis methods are also suitable for the preparation of oligonucleotides if they are removed from the support surface.

Some time ago, another method was developed for the nucleic acid-chip synthesis: the light-controlled chip synthesis. The phosphite amides (A, C, G, T) used in the light-controlled synthesis have the same chemical structure as in the "normal" DNA synthesis on a commercial DNA synthesizer, the only difference being that the 5'-acid-labile dimethoxytrityl protecting group is replaced by a photolabile protecting group which may be at position 5' or 3'. This leads to the following reaction course on the DNA chip synthesizer:

| | |
|---|---|
| (1) Irradiation | cleavage of the temporary photolabile protecting group by irradiation using light of corresponding wavelength; |
| (2) condensation | the phosphite amide corresponding to the target sequence is condensed onto the released hydroxyl function; this is done with the aid of the acidic catalyst (tetrazole); |
| (3) oxidation | the unstable phosphite triester linkage (P-III) is converted by oxidation with iodine into a stable phosphorus triester (P-V); |
| (4) capping | the hydroxyl functions which did not react in the preceding step shall be trapped by an acetylation step (acetic anhydride + N-methylimidazole); this shall prevent uncontrolled growth of the DNA strand. |

Steps (1) to (4) are then repeated until the target sequence has been obtained.

The initiator nucleoside is usually not found on the support, so that the condensation step is started with here. As soon as the target sequence has been obtained, the phosphate protecting groups and the protecting groups of the exocyclic amino functions have to be split off as well.

This is done by means of ammonia but under milder conditions (2 h) so that the DNA strands synthesized on the chip are not split off the support. This becomes possible by using more labile protecting groups than employed for the common synthesis of CPG materials as protecting groups of the exocyclic amino functions. The DNA chip is then simply removed from the ammoniacal solution, washed with water and can immediately be used for hybridization experiments.

The quality of the DNA chip synthesis is determined in the light-controlled method not only by condensation alone but, above all, by the efficiency of the cleavage of the photolabile protecting groups which only in rare cases is as effective as the cleavage of the dimethoxytrityl protecting group by means of acid. Since yields of up to 95–99% can usually be achieved in the condensation step, the quality of the DNA chip is determined more or less by the efficiency of the photoprotecting group cleavage.

WO 96/18634 and WO 97/44345 are special photolabile protecting groups of the 2-(2-nitrophenyl)ethyl type which shall be suitable for the preparation of oligonucleotides on a DNA chip. However, the inventors have already found out that it is very difficult to split off the photolabile protecting groups shown in these applications by common methods and that the preparation of DNA or RNA chips is not very efficient. Moreover, it turned out that due to their inferior quality chips prepared in such a way cannot be detected by means of fluorescence, which is current standard to detect DNA chips. Probe labeling by means of radiography would be required for the detection of these chips. This is, however, not usable for commercial exploitation.

The object of the present invention consists in providing a method by means of which high-quality biochips, in particular DNA or RNA chips, can be produced.

This object is achieved by the subject matters defined in the claims.

SUMMARY OF THE INVENTION

The present invention is achieved by a method for the light-controlled biochip synthesis in which photolabile protecting groups of the 2-(2-nitrophenyl)ethyl type are used. The irradiation step common in the light-controlled chip synthesis is carried out in the presence of a base.

BRIEF DESCRIPTION OF THE FIGURES

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE INVENTION

Figure 1:
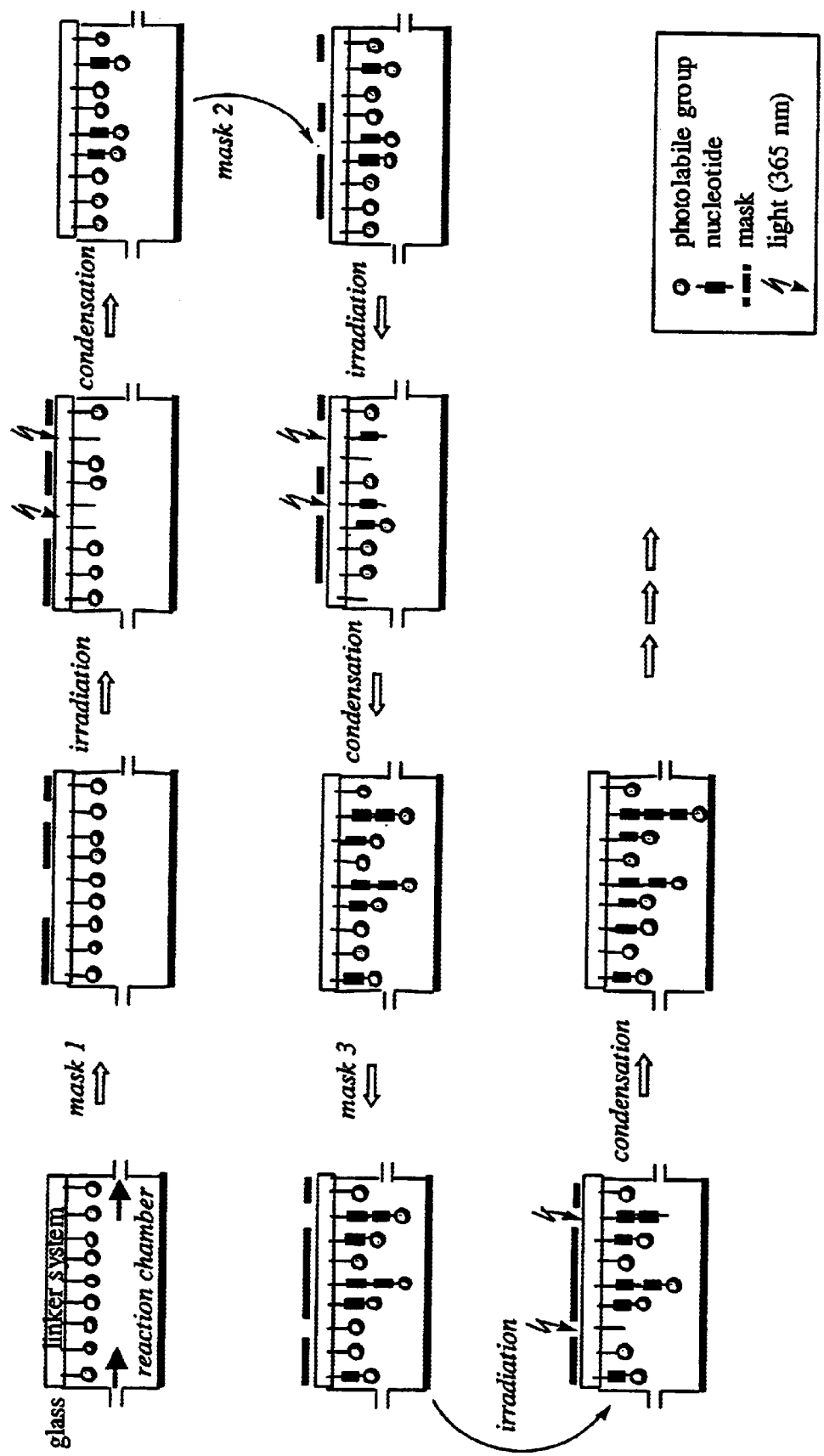
FIG. 1 shows the reaction scheme for the DNA-chip synthesis for building up an 8-mer (CAGGTCGC) on a glass support surface.

The method according to the invention for the light-controlled biochip synthesis offers the advantage that the efficient cleavage of photolabile protecting groups of the 2-(2-nitrophenyl)ethyl type can be achieved. The photolabile protecting groups have preferably the following formula:

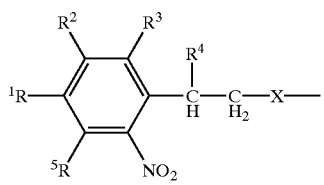

(1)

$R^1$=H, $NO_2$, CN, $OCH_3$, halogen, alkyl or alkoxyalkyl having 1 to 4 C atoms $R^2$=H, $OCH_3$, alkyl residue having 1 to 4 C atoms or optionally substituted aryl residue $R^3$=H, F, Cl, Br, $NO_2$, alkyl residue having 1 to 4 C atoms or optionally an aryl residue or an aliphatic acyl residue having 2 to 5 C atoms, $R^4$=H, halogen $OCH_3$, alkyl residue having 1 to 4 C atoms or optionally substituted aryl residue $R^5$=H, $NO_2$, CN, $OCH_3$, halogen, alkyl or alkoxy alkyl having 1 to 4 C atoms or optionally substituted aryl residue X=$SO_2$ (sulfonyl), OCO (oxycarbonyl)

It is particularly preferred to use the protecting groups NPPOC or CNPOC which have the following formula, NPPOC being most preferred:

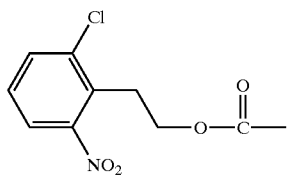
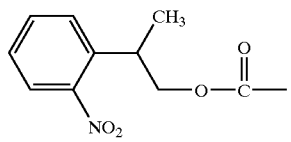

The above protecting groups may be used generally for protecting hydroxyl or amino functions on nucleic acid derivatives, peptides, proteins, antibodies or other biomolecules, preferably for protecting the hydroxyl functions in nucleic acid derivatives, in particular for protecting the 5'-OH position or the 3'-OH position in nucleic acid derivatives. As mentioned already in connection with the above prior art, they shall be used in particular for the synthesis of high-quality DNA or RNA chips, which has not yet succeeded since the step of photodeprotection by irradiation does not proceed efficiently enough. High-quality DNA chips are meant to be those obtained when the yield in each step is as high as possible during the light-controlled synthesis.

According to the invention a biochip is understood to mean biomolecules, such as DNA, RNA, nucleic acid analogs (e.g. PNA, LNA), proteins, peptides, antibodies, synthesized on a support, the three former groups being preferred.

According to the invention any support or matrix, common in this field, can be used for the biochip production. These are in particular glass, sheets or membranes made of polypropylene, nylon, cellulose, cellulose derivatives (e.g. cellulose acetate, mixed cellulose phosphate group. In a preferred embodiment the support surfaces have a derivatization according to German patent application 198 53 242.3.

The steps condensation, oxidation and capping are carried out as usual in the method for light-controlled biochip synthesis according to the invention (Fodor et al., Science 1991, 251, page 767 et seq.). According to the invention the first step of synthesis, namely the irradiation, is however carried out by adding bases, preferably strong bases, in particular non-nucleophilic bases, which in cooperation with the light used for the irradiation leads to a surprisingly effective cleavage of the protecting groups. The invention provides for the fact that by admixing bases during the irradiation a higher yield can be achieved on the solid support material. In this connection, it must be stressed that an efficient cleavage of the protecting groups on the solid support material cannot be achieved by either the influence of light without base addition or base addition alone. Correspondingly, the method according to the invention makes use of a well defined system consisting of light action in combination with base addition for a successful light-controlled parallel synthesis of DNA arrays on the solid support material.

For example, the irradiation in the presence of 0.05 M diisopropylethylamine in acetonitrile represents such an exemplary successful combination of light action and base addition. The NPPOC photoprotecting group cannot be cleaved efficiently by irradiation in various solvents without base addition (e.g. in acetonitrile alone) nor can it be abstracted by treatment with 0.05 M diisopropylethylamine in acetonitrile without the action of light. This means that only the combination of a base together with the action of light effects an efficient cleavage of the protecting groups.

In a preferred embodiment bases, such as DBU (1,8-diazabicyclo[5.4.0]undec-7-ene), diisopropylethylamine, N-methylmorpholine, N-methylimidazole, piperidine are suitable as addition during the irradiation. The secondary or tertiary bases known to the person skilled in the art, e.g. DBN (1,5-diazabicyclo[4.3.0]none-5-ene), triethylamine, DABCO, 2,6-lutidine, collidine, morpholine, diisopropylamine, triethylamine, are also usable.

The irradiation may take place under common conditions. The wavelength of irradiation depends on the protecting group used. The person skilled in the art is familiar with the suitable wavelengths. A 5-minute irradiation with a 100 W Hg lamp at a wavelength between 320 and 380 nm, preferably at 365 nm, is suitable for splitting off the NPPOC or CNPOC protecting group.

The amount of base present during the irradiation varies between 0.01 M and 1.0 M and depends, of course, on the base strength. It proved efficient to use 0.03 to 1 M (preferably 0.05 to 0.5 M) DBU in acetonitrile, 0.03 to 0.8 M (preferably 0.05 M) diisopropylethylamine in acetonitrile or 0.03 to 1 M (preferably 0.5 M) piperidine in acetonitrile.

In other preferred embodiments, modifications occur in the other steps of photolithographic nucleic acid chip synthesis. It turned out to be preferable to use pyridine hydrochloride (preferably 0.1 to 1.0 M, more preferably 0.5 M, in actonitrile) in place of tetrazole as a catalyst for the condensation. Moreover, it was found that the formerly common addition of THF can be dispensed with for the oxidizing agent. A reduction of the common iodine amount also proved advantageous for the oxidizing step. Furthermore, the common THE was replaced by acetonitrile in the capping reagent. As can be proved, the capping procedure may fully be omitted without a negative effect on the quality of the chips resulting. Thus, the synthesis can be accelerated considerably.

The invention is described in more detail by means of the below example:

EXAMPLES

Example 1

Light-controlled (Photolithographic) DNA-chip Synthesis Using NPPOC as a Protecting Group The DNA chip synthesis was carried out in analogy to the known method by Fodor et al. (Science 1991, 251, p. 767 et seq.) on a glass surface as the support. The reaction course is shown in FIG. 1 by way of diagram. NPPOC-protected phosphite amides (company of Nigu-Chemie, Waldkraiburg) were used as nucleosides.

A DNA chip synthesizer program is composed of individual subroutines which correspondingly represent the individual synthesis steps for the oligonucleotide synthesis according to the phosphite amide chemistry and are processed one after the other. The cycle is as follows:

| | |
|---|---|
| (1), (3), (5), (9), (12) = M-wash | subroutine which is interposed between all of the other ones for the purpose of washing the reaction flow chamber and removing residues from the preceding step |
| (2) = M-coup | linkage of the new phosphite amide building block on the photo-released 5'-OH function of the preceding building block at this position |
| (3) = M-ox | labile phosphite triester function is oxidized by iodine to give the phosphate triester |
| (6) = M-dry | actuates the opening of the shutter and thus the irradiation of the reaction flow chamber using light. An external electronic circuit which is operated by the DNA synthesizer via a potential-free signal actuates the opening. This circuit serves for setting how long the shutter remains open and thus how long irradiation takes place. The irradiation procedure is described in more detail below |
| (7), (10) = M-irrad. | The irradiation solution is pumped into the reaction flow chamber. In some cases, the irradiation solution contains a base (DBU, piperidine, . . .) |
| (8), (11) = M-waitdr. | wait loop of 110 sec. (may be adjusted as desired), both subroutines together yield a desired irradiation period (here: 5 minutes) |

(1) M-wash
(2) M-coup
(3) M-wash
(4) M-ox
(5) M-wash
(6) M-dry
(7) M-irrad.
(8) M-waitdr.
(9) M-wash
(10) M-irrad.
(11) M-waitdr.
(12) M-wash The irradiation (5 minutes of irradiation with a 100 W Hg lamp, at 365 nm) was carried out as follows:
  opening of the shutter (thus starting of irradiation in the reaction chamber),
  flushing of the reaction flow chamber with irradiation solution,
  the irradiation solution is pumped out of the chamber after 150 seconds,
  short washing of the chamber using acetonitrile,
  another flushing of the reaction flow chamber with irradiation solution—after a total of 300 seconds the shutterdcloses (the irradiation is terminated),
  the irradiation solution s pumped out of the chamber,
  thorough washing of the chamber using acetonitrile.

The subsequent steps of condensation, oxidation and capping remained unchanged as compared to the reaction course of the prior art (Weiler et al, Analytical Biochemistry, 243, pp. 218–227 (1996)) or showed the modifications described on page 8.

The irradiation solutions contained 0.05 M DBU, 0.5 M DBU, 0.05 M diisopropylethylamine or 0.05 M piperidine, each in acetonitrile.

Chips using NPPOC-protected phosphite amides but without using base or with using not enough base in the irradiation step were produced as a control. The irradiation solutions contained in these cases 0.005 M DBU in acetonitrile, pure acetonitrile or 10% $H_2O$/MeOH. In one case, the irradiation was carried out in a dry state.

Figure 2:
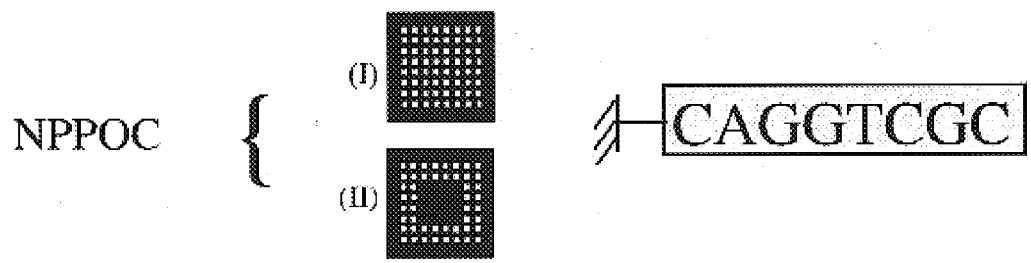
FIG. 2 shows the NPPOC photochemistry; conventional method (without base addition or not enough base) results in no DNA chip synthesis.
Figure 2:
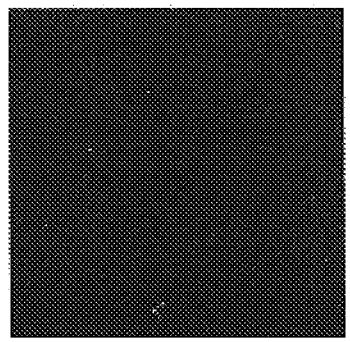
Figure 2:
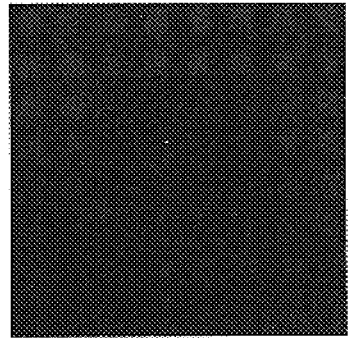
Figure 2:
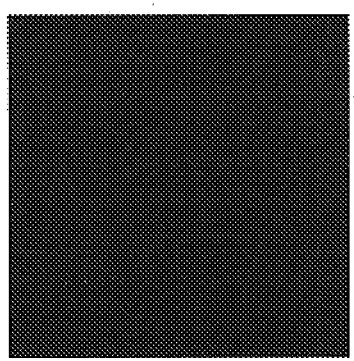
Figure 2:
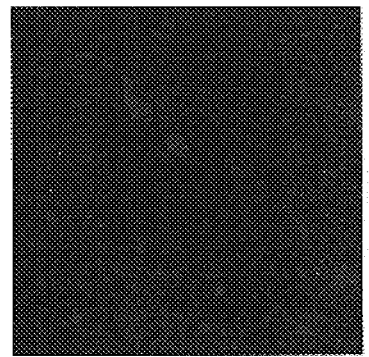
Figure 3:
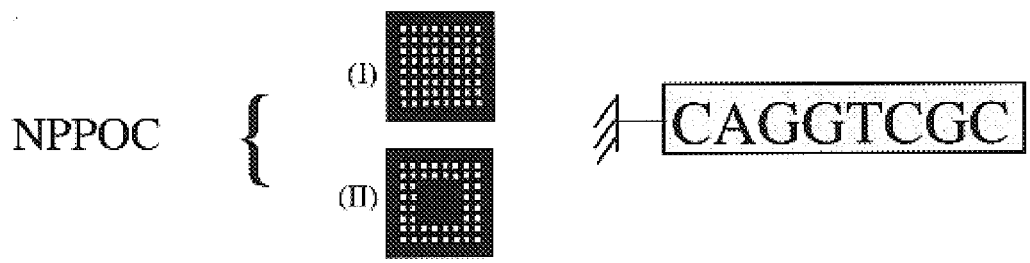
FIG. 3 shows the NPPOC photochemistry; irradiation with the addition of bases results in effective DNA chip synthesis.
Figure 3:
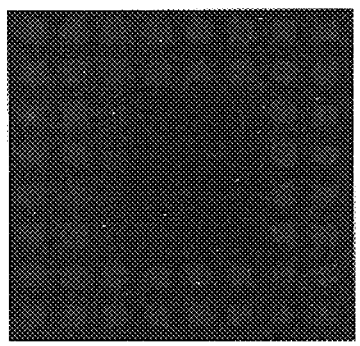
Figure 3:
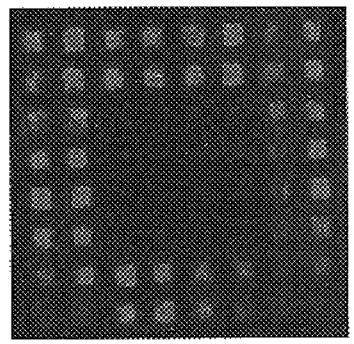
Figure 3:
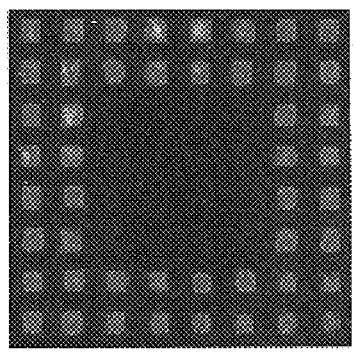
Figure 3:
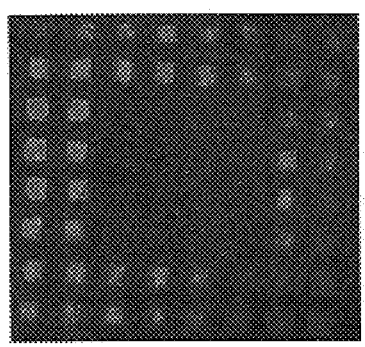

When comparing FIGS. 2 and 3, which represent a fluorescence analysis of the produced chips, it has to be noted that in the irradiation an effective DNA chip synthesis is only possible with base additive, i.e. a pattern corresponding to mask II can only be detected there. No chip synthesis is obtained when there is no or not enough base addition, which is expressed by the totally blackened images. It is thus proved that the addition of the base contributes actively to the abstraction of the photo-protecting group of the type of formula (I).

What is claimed is:

1. A method for synthesizing a light-controlled biochip comprising the step of carrying out an irradiation step common for a photolithographic chip in the presence of a base, wherein photolabile protecting groups of the 2-(2-nitrophenyl)ethyl type are used.

2. The method according to claim 1, wherein the base is a secondary or tertiary base.

3. The method according to claim 1 or 2, wherein the base is selected from the group consisting of 1, 8-diazabicycloundec-7-ene, 1, 5-diazabicycionone-5-ene, diisopropylethylamine, pyridine, piperidine, triethylamine, diisopropylamine, N-methylmorpholine, 2,6-lutidine, collidine, N-methylimidazole, DABCO, and N,N-dimethylaminopyridine.

4. The method according to claim 3, wherein the base is used in a concentration of 0.01 to 1 M.

5. The method according to claim 1 or 2, wherein the photolabile protecting group has the formula (I):

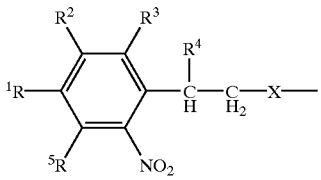

(1)

$R^1$=H, $NO_2$, CN, $OCH_3$, halogen, alkyl or alkoxyalkyl having 1 to 4 C atoms, $R^2$=H, $OCH_3$, alkyl residue having 1 to 4 C atoms or optionally substituted aryl residue, $R^3$=H, F, Cl, Br, $NO_2$, alkyl residue having 1 to 4 C atoms or optionally an aryl residue or an aliphatic acyl residue having 2 to 5 C atoms, $R^4$=H, halogen, $OCH_3$ alkyl residue having 1 to 4 C atoms or optionally substituted aryl residue, $R^5$=H, $NO_2$, CN $OCH_3$, halogen, alkyl or alkoxyalkyl having 1 to 4 C atoms or optionally substituted aryl residue, and X=$SO_2$ (sulfonyl), OCO (oxycarbonyl).

6. The method according to claim 5, wherein the photolabile protecting group is NPPOC or CNPOC.

7. The method according to claim 1 or 2, wherein the biochip is a nucleic acid chip or nucleic acid analog chip.

8. The method according to claim 7, wherein the nucleic acid chip is a DNA or RNA chip.

9. The method according to claim 7, wherein the nucleic acid analog chip is a PNA or LNA chip.

10. The method according to claim 1, further comprising carrying out a condensation step common in a light-controlled chip synthesis with pyridine hydrochloride as a catalyst.

* * * * *